(12) United States Patent
Carn

(10) Patent No.: US 8,235,594 B2
(45) Date of Patent: Aug. 7, 2012

(54) ALIGNMENT FIXTURE FOR X-RAY IMAGES

(76) Inventor: Ronald M. Carn, Redding, CA (US)

(*) Notice: Subject to any disclaimer, the term of this patent is extended or adjusted under 35 U.S.C. 154(b) by 142 days.

(21) Appl. No.: 12/906,394

(22) Filed: Oct. 18, 2010

(65) Prior Publication Data
US 2011/0103556 A1    May 5, 2011

Related U.S. Application Data

(60) Provisional application No. 61/257,316, filed on Nov. 2, 2009.

(51) Int. Cl.
*A61B 6/08* (2006.01)
(52) U.S. Cl. .......................... 378/205; 378/163
(58) Field of Classification Search .................. 378/205, 378/163, 165, 37
See application file for complete search history.

(56) References Cited

U.S. PATENT DOCUMENTS

| | | | |
|---|---|---|---|
| 2,293,324 A | 8/1942 | Vladeff | |
| 2,650,308 A | 8/1953 | Catlin | |
| 2,790,084 A | 4/1957 | O'Dell et al. | |
| 3,577,160 A | 5/1971 | White | |
| 3,812,842 A | 5/1974 | Rodriguez | |
| 3,936,641 A * | 2/1976 | Heimur | 5/637 |
| 3,941,127 A | 3/1976 | Froning | |
| 4,915,112 A | 4/1990 | Singer | |
| 4,971,060 A | 11/1990 | Schneider et al. | |
| 5,020,088 A | 5/1991 | Tobin | |
| 5,606,590 A | 2/1997 | Petersen et al. | |
| 5,778,043 A | 7/1998 | Cosman | |
| 6,131,690 A | 10/2000 | Galando et al. | |
| 6,178,229 B1 | 1/2001 | Ko | |
| 6,424,694 B1 * | 7/2002 | Molteni et al. | 378/38 |
| 6,644,852 B2 | 11/2003 | Crain | |
| 6,717,174 B2 | 4/2004 | Karellas | |
| 7,341,376 B2 | 3/2008 | Birdwell | |
| 7,344,307 B2 | 3/2008 | Yatsenko et al. | |
| 7,482,601 B2 | 1/2009 | Lewis et al. | |
| 2004/0086082 A1 | 5/2004 | Foos et al. | |
| 2006/0285641 A1 | 12/2006 | Scherch | |
| 2007/0100225 A1 | 5/2007 | Maschke | |

FOREIGN PATENT DOCUMENTS
EP    1 005 832 B1    10/2006

* cited by examiner

*Primary Examiner* — Hoon Song
(74) *Attorney, Agent, or Firm* — Lowry Blixseth LLP; Stuart O. Lowry; Scott M. Lowry

(57) ABSTRACT

An alignment fixture for taking X-ray images of a patient, such as an image of the patient's hip region preparatory to hip arthroplasty. The alignment fixture comprises multiple support legs for resting on the patient at known positions, such as upon known bony prominences, in combination with aiming marks used for anatomically aligning the patent's pelvis under an X-ray beam. A ruled grid plate on the fixture is adjustably positioned between an image beam source and the patient, as a function of patient thickness in the pelvic region, so that a ruled grid overlays the anatomical region of interest and exhibits an apparent parallax image magnification corresponding with the parallax image magnification of a centerline of the anatomical region, such as the hip joint. X-ray images taken by use of the alignment fixture can be viewed and/or scaled to select a properly sized prosthesis for the specific patient.

22 Claims, 6 Drawing Sheets

ALIGNMENT FIXTURE FOR X-RAY IMAGES

BACKGROUND OF THE INVENTION

This invention relates generally to an improved alignment fixture and related method of use for taking X-ray images of a selected anatomical region of a patient, such as the pelvis and hip region preparatory to hip arthroplasty or hip replacement surgery, wherein the fixture aligns the pelvis in the X-ray beam and a ruled grid appears in the X-ray image to overlie the anatomical region of interest with a known parallax magnification corresponding with the parallax magnification of the anatomical region. Accordingly, X-ray images taken with the improved alignment fixture consistently align the pelvis and the projected grid and can be scaled quickly and easily for use in selecting a prosthesis size suitable for the specific patient.

X-ray imaging is a known medical technique wherein X-rays are generated from a beam source to pass through a selected anatomical region of a patient. Some of the X-rays are absorbed by the patient whereas others pass through the patient to impact a sheet of X-ray film or recording media, thereby producing a shadow-type image of the anatomical region of interest. In this regard, in many X-ray systems, the X-rays are generated from an essentially point source and travel downwardly through the selected anatomical region of the patient to impact the X-ray film or recording media underlying the patient. This X-ray imaging arrangement inherently produces magnification of the selected anatomical region by parallax, due to the fact that the X-ray beam expands as it travels from the point source, and the anatomical region is not located in the same plane as the X-ray film or recording media. Accordingly, the actual X-ray image does not correspond exactly with the size of the patient's anatomical structure. While this parallax magnification is not a problem in some X-ray imaging applications, such as diagnosis of a bone fracture or the like, it can be particularly problematic in an X-ray image taken prior to a surgical procedure involving implantation of a prosthesis, such as arthroplastic hip replacement surgery, wherein a primary reason for taking the pre-surgery X-ray image is to enable the surgeon to plan the surgery and to select a prosthesis of suitable size and design for the specific anatomy of the surgical patient.

A variety of devices and systems have been developed in the prior art in an attempt to accommodate or compensate for parallax image magnification in an X-ray image taken preparatory to a prosthesis implantation surgery. Such prior art devices and systems generally relate to placement of a ruled grid in overlying relation with the patient anatomy, so that the ruled grid can provide an indication of actual anatomical size. However, the ruled grid cannot be physically located at the same vertical plane as the patient's anatomical region, particularly when that anatomical region comprises a structure such as a hip joint located deep within the patient. For this reason, such prior art devices and systems have generally required undue estimation when used to indicate the size of a deep anatomical structure, such as a hip joint. Accordingly, such prior art devices and systems have relied for accuracy largely upon the technique and skill of an individual X-ray technician, whereby the actual placement of the ruled grid in relation to the anatomical region of interest has been subject to an unacceptable margin of error. As a result, confident pre-surgical prosthesis size determination based upon a pre-surgical X-ray image has remained an elusive objective. Prior art does not address aligning the pelvis in the X-ray beam which is integral with consistent and accurate planning of the hip or pelvis surgery.

There exists, therefore, an on-going and substantial need for an improved X-ray imaging alignment fixture that is relatively simple and easy-to-use, without requiring undue skill by the individual X-ray technician, to permit quick and easy alignment of the pelvis in the X-ray beam and scaling of a resultant X-ray image in relation to a ruled grid, and thereby permit confident selection by an examining surgeon or the like of an appropriately sized prosthesis for a specific patient. The present invention fulfills these needs and provides further related advantages.

SUMMARY OF THE INVENTION

In accordance with the invention, an alignment fixture is provided for quickly and easily taking X-ray images of a patient, such as an X-ray image of the patient's pelvis and hip region preparatory to hip arthroplasty or hip replacement surgery. The alignment fixture comprises a frame having multiple support legs for resting on the patient at known positions, such as upon known bony prominences, in combination with a ruled grid on a grid plate which is adjustably positioned between an image beam source and the patient as a function of specific measured patient thickness, such as the thickness of the patient's pelvic region. The fixture supporting the ruled grid has at least two alignment sites for aligning the pelvis in the X-ray beam. As a result, the ruled grid overlies the anatomical region of interest to appear in an X-ray image with a known parallax image magnification corresponding with the parallax image magnification of a center of the anatomical region of interest, such as the patient's hip joint. X-ray images taken by use of the alignment fixture can be viewed and/or scaled for confidently selecting a properly sized prosthesis for the specific patient.

The alignment fixture comprises a relatively simple device adapted for interactive patient retention and accurate alignment over the selected anatomical region, with the patient lying, for example, on a table between an X-ray beam source and a sheet of X-ray film or recording media on the table.

In one preferred form, the alignment fixture comprises a tripod frame having three legs depending from an upright frame post. The three frame legs are positioned for interactive patient retention on a respective trio of bony prominences on the patient, such as the anterior superior iliac spines and the symphysis pubis in the case of a hip replacement patient. The three tripod legs preferably include laterally or substantially horizontally turned feet for stable support respectively upon this trio of bony prominences, wherein the tripod feet may additionally include radio-opaque markers formed in an otherwise radio-transparent frame material (such as plastic) for assisting in placing the fixture frame onto patients of different typical sizes, such as a small-framed, medium-framed, or large-framed patient. These radio-opaque feet markers may appear in a resultant X-ray image to assist in confirming proper fixture alignment over the patient's skeletal structure.

The grid plate is mounted onto a vertically extending frame post in a manner accommodating vertical positional adjustment. The grid plate comprises, in the case of a hip patient, a grid plate having a pair of ruled grids each having a noted size spacing (such as about 1 centimeter or the like) positioned for respectively overlying the patient's hip joints, when the frame legs are supported upon the patient's bony prominences as described above.

Vertical adjustment of the grid plate is performed by first measuring the thickness of the selected anatomical region of the patient, such as the pelvic region in the case of a hip patient. From a knowledge of the relationship between patient thickness and a centerline through the anatomical region of interest, such as the hip joint, the grid plate is adjustably vertically positioned on the frame post in a manner so that the pair of ruled grids respectively overlie the anatomical region such as the patient's hip joints. In this regard, the radio-opaque feet markers assist in adjusting the position of the grid plate according to patient size. In addition, radio-opaque alignment marks such as fixture cross hairs formed on an upper alignment arm of the fixture frame and also on the grid plate spaced therebelow assist in aligning the patient and fixture relative to the X-ray beam source.

Parallax magnification of the ruled grids on the grip plate and of the selected anatomical region, such as the hip joints, occurs by virtue of X-ray beam expansion as the X-rays travel downwardly from the substantially point beam source to impact the X-ray film or recording media disposed below the patient, according to the mathematical law of cosines. In this regard, the specific parallax magnification for the ruled grids and for the anatomical region (such as the hip joints) is different because the grid plate and the selected anatomical region are located at different distances from the sheet of X-ray film underlying the patient. However, by controlling the actual spacing between radio-opaque grid markers (lines) of the ruled grids, and by adjusting the vertical position of the grid plate in accordance with the specific thickness of the patient, such as the specific pelvic thickness as measured, e.g., with calipers or the like, the ruled grids are projected onto the X-ray film with an apparent parallax magnification corresponding with the parallax magnification of the anatomical region, such as the patient's hip joint.

Accordingly, in one preferred form of the invention, the ruled grids each include radio-opaque grid lines or the like, with an actual known line-to-line distance less than a known as-marked measurement. In the preferred form, the marked measurement comprises a 1 centimeter (cm.) spacing, but the actual line spacing is less—about 0.6 cm. By appropriately adjusting the vertical position of the grid plate as a function of measured patient thickness, these spaced grid lines are projected onto the X-ray film or recording media in overlying relation to the selected anatomical region, such as the hip joints, with an parallax image magnification corresponding with the actual magnification of the anatomical region. By way of specific example, for an X-ray image having parallax magnification of the hip joints of about 125%, the grid lines will overlie the magnified image with an actual line spacing of about 1.25 cm. The resultant X-ray image can be scaled and viewed quickly and easily by a surgeon or the like for pre-surgery selection of a prosthesis of appropriate size for the particular patient.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 7:
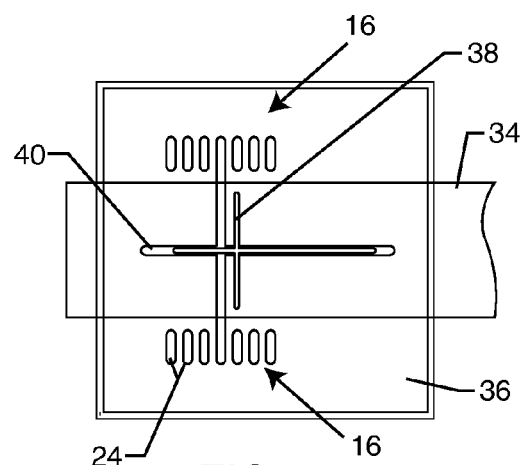
FIG. 7 is an enlarged top plan view of aiming marks on the alignment fixture taken generally on the line 7-7 of FIG. 6, and showing the aiming marks in slight misalignment.
Figure 8:
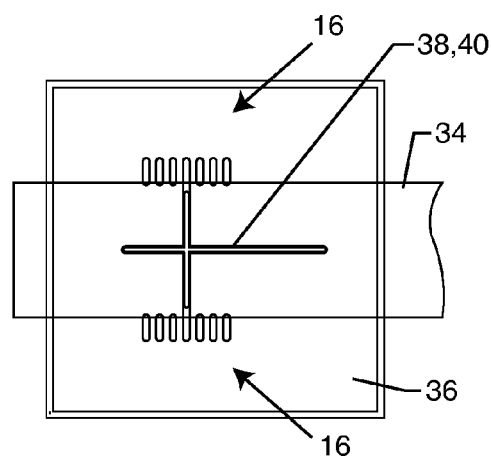
FIG. 8 is an enlarged top plan view similar to FIG. 7, but illustrating the aiming marks in vertical alignment.
Figure 9:
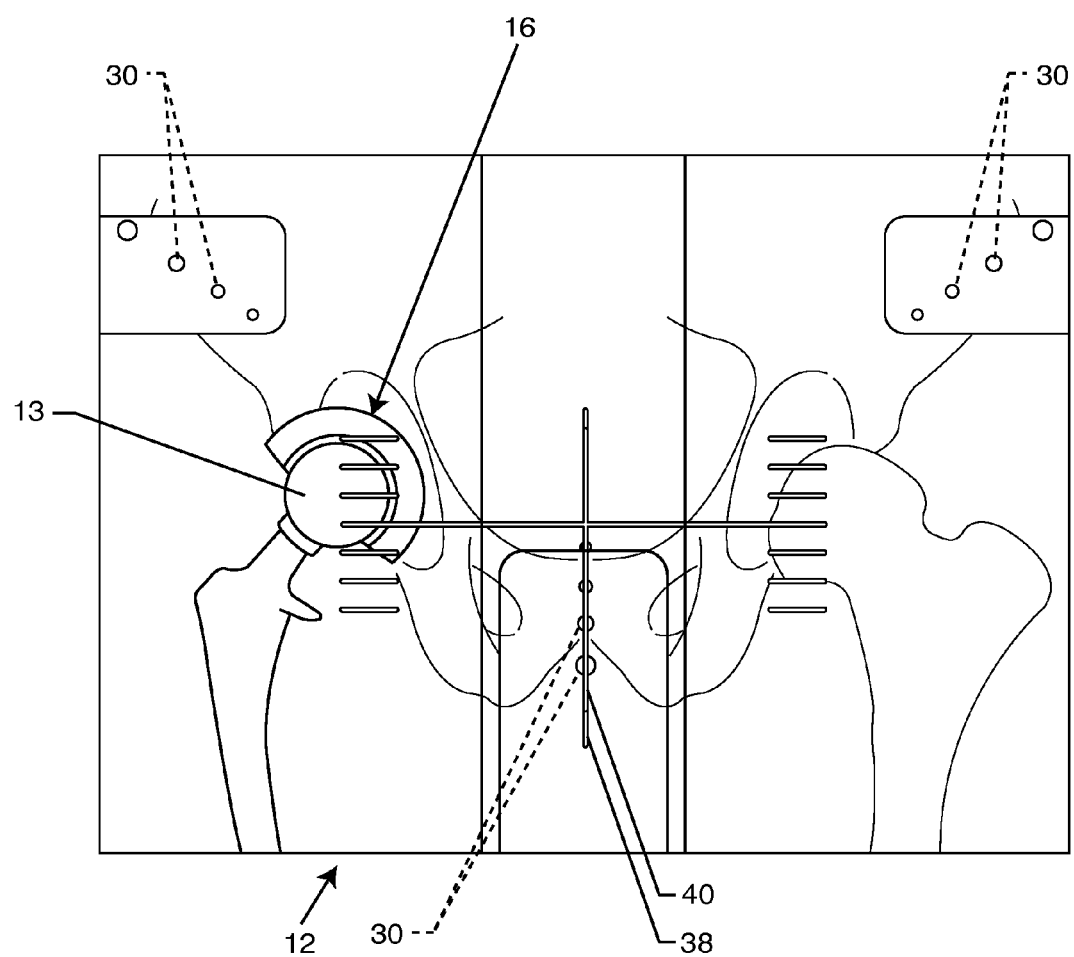
FIG. 9 is an X-ray image of a patient's pelvic region using the alignment fixture of the present invention.

As shown in the exemplary drawings, an improved alignment fixture referred to generally by the reference numeral 10 in FIGS. 1-2 and 4-8 is provided for taking an X-ray image 12 (FIG. 9) of a patient 14 (FIGS. 3-6). The alignment fixture 10 is particularly designed for taking an X-ray image 12 preparatory to a prosthesis installation surgery (although FIG. 9 shows a pair of hip replacement prostheses 13 already installed), so that a prosthesis 13 of the correct size can be selected with confidence prior to the surgical procedure. In this regard, the alignment fixture 10 positions at least one radio-opaque ruled grid 16 at a selected vertical position above the patient 14, in accordance with the specific measured thickness (FIG. 4) of a selected anatomical region of the patient 14, such as the pelvic region in the case of a hip replacement patient. The vertical position of the ruled grid 16 is adjustably selected to overlay the selected anatomical region, such as a hip joint or hip joints, to provide a known parallax magnification corresponding with the parallax magnification of the anatomical region, thereby permitting quick and easy scaling and viewing of a resultant X-ray image 12 for confident pre-surgical selection of an appropriate-sized prosthesis for the specific patient.

In conventional X-ray imaging systems, X-rays are generated from a substantially point beam source 18 (FIG. 6) disposed above the patient 14 lying on an X-ray table 20 in a position with the selected anatomical region, such as the hip joint or joints, over a sheet 22 of X-ray film or other suitable recording media. X-rays thus pass downwardly from the beam source 18 and pass through the patient 14 before impacting the X-ray film 22 or the like. A portion of the generated X-rays are absorbed by the selected anatomical region of the patient, resulting in the X-ray image 12 (FIG. 9) which can be viewed for medical analysis. Importantly, the generated X-rays expand from the beam source to result in magnification of the anatomical region by parallax, due to the fact that the selected anatomical region (such as the hip joints) is spaced above the X-ray film 22 or the like, with the specific image magnification being determined by the mathematical law of cosines. Accordingly, use of the resultant X-ray image 12 for pre-surgical selection of a prosthesis size suitable for a unique patient 14 inherently requires scaling of the X-ray image 12 to compensate for this parallax image magnification.

The alignment fixture 10 of the present invention is interactively retained in the desired alignment position by the patient 14. The alignment fixture 10 provides the ruled grid or grids 16 to overlay the selected anatomical region of the patient 14 in the produced X-ray image, wherein this ruled grid 16 includes radio-opaque spaced grid lines 24 or the line with a marked inter-line spacing, such as an inter-line spacing of about 1 centimeter (cm.). However, the actual inter-line spacing is less than the marked spacing, since the ruled grid 16 is located above the patient 14 and thereby is located further from the X-ray film 22 than the selected anatomical region and thus is magnified by a comparatively greater amount. The specific vertical position of the ruled grid 16 above the patient 14 is adjustably selected according to the measured thickness of the patient 14 at the selected anatomical region, such as the pelvic region, so that the grid lines 24 are magnified to provide a true as-marked inter-line spacing (such as 1 cm.) at the specific anatomical region of interest. In this regard, the location of a hip joint centerline is empirically determined as a function of measured pelvic region thickness of the patient (FIG. 3), within a small and acceptable margin of error. Thereafter, as the hip joint is magnified by parallax due to the distance between the hip joint center and the X-ray film 22, the ruled grid 16 is also magnified by the same amount, whereby the resultant X-ray image includes the ruled grids 16 in overlying relation to the hip joints with an apparent common magnification to permit easy viewing and scaling to select prosthesis size.

Figure 1:
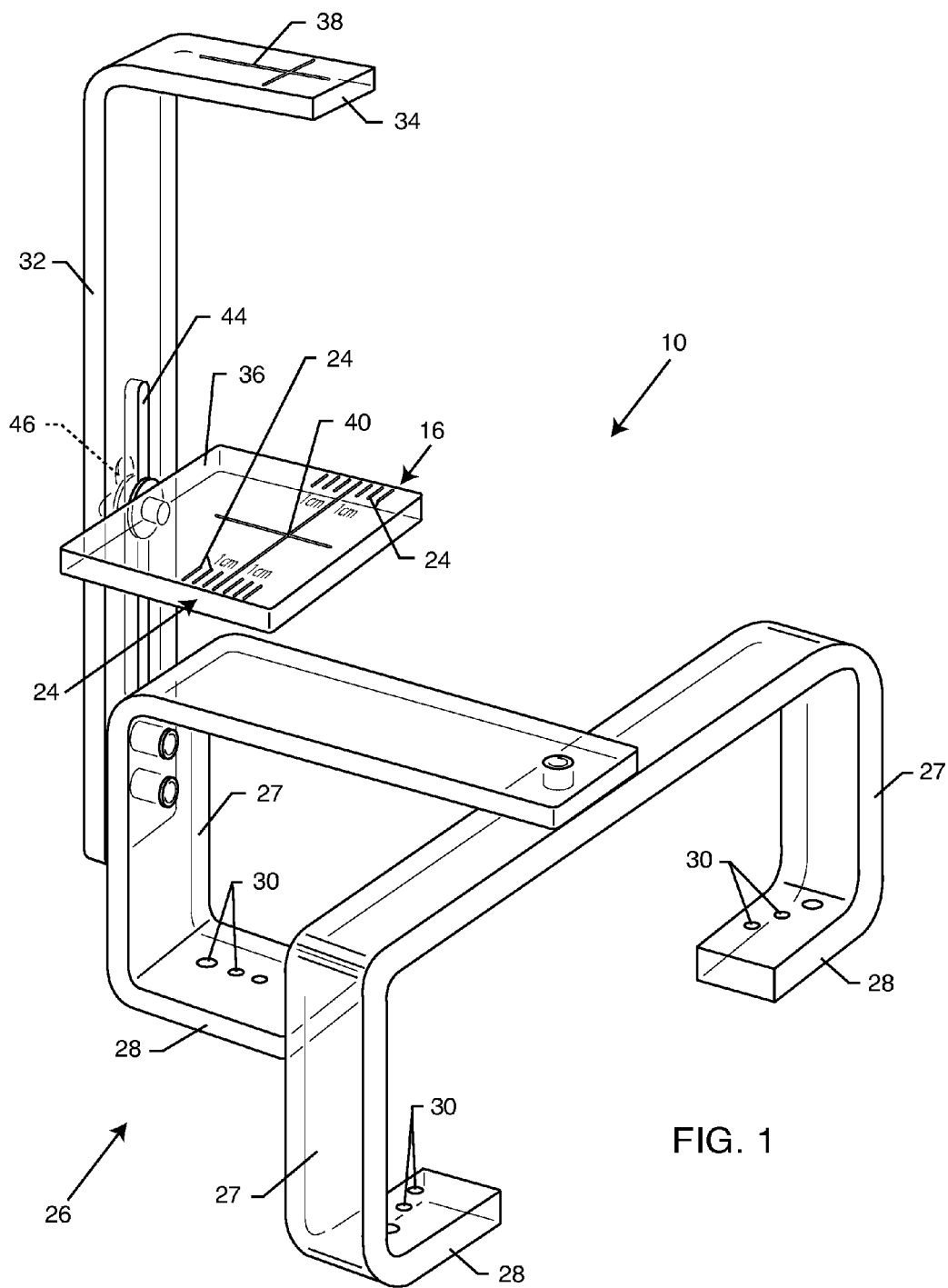
FIG. 1 is a front perspective view showing the alignment fixture of the present invention in accordance with one preferred form.
Figure 2:
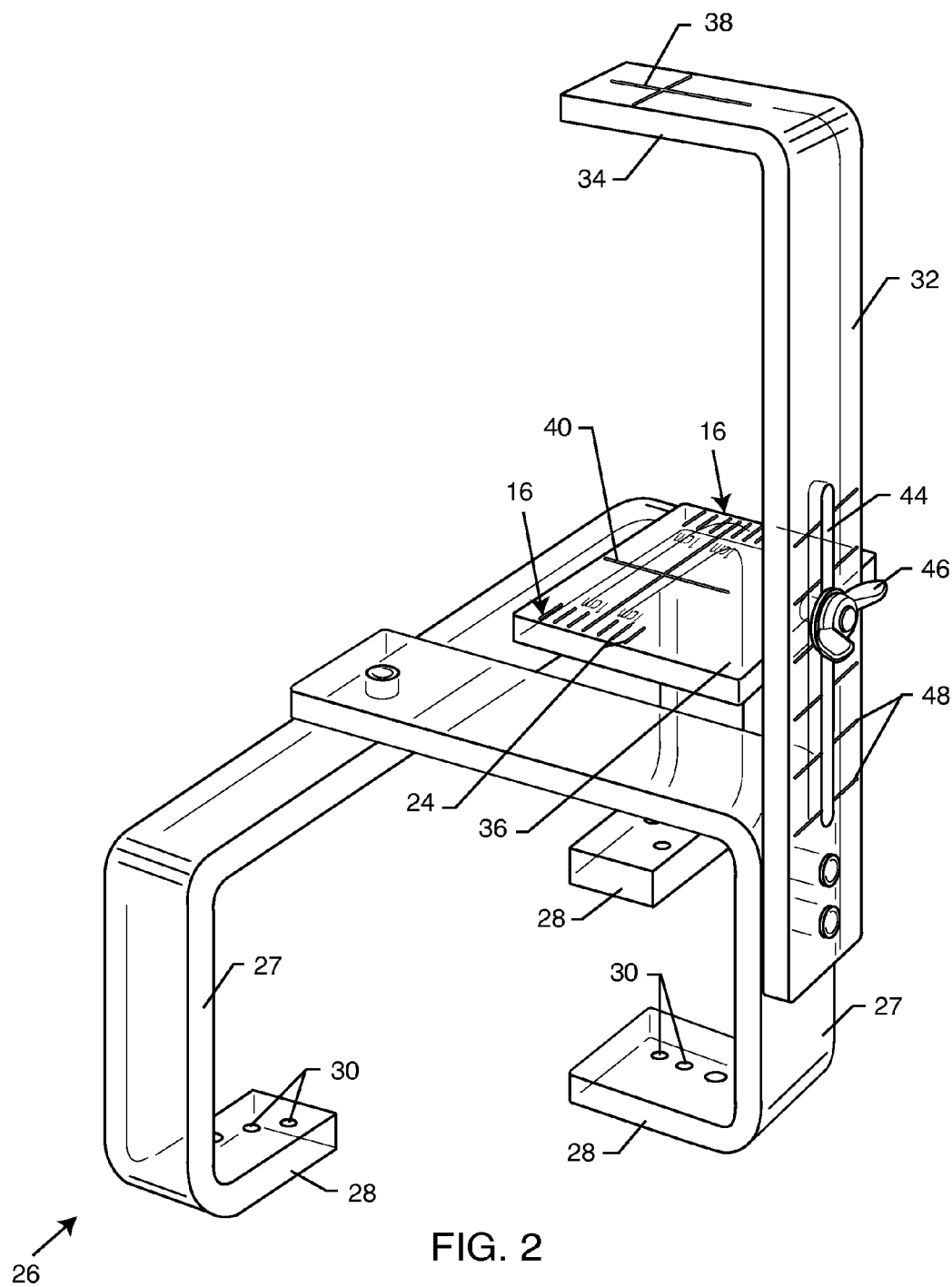
FIG. 2 is a rear perspective view showing the alignment fixture of the FIG. 1.
Figure 3:
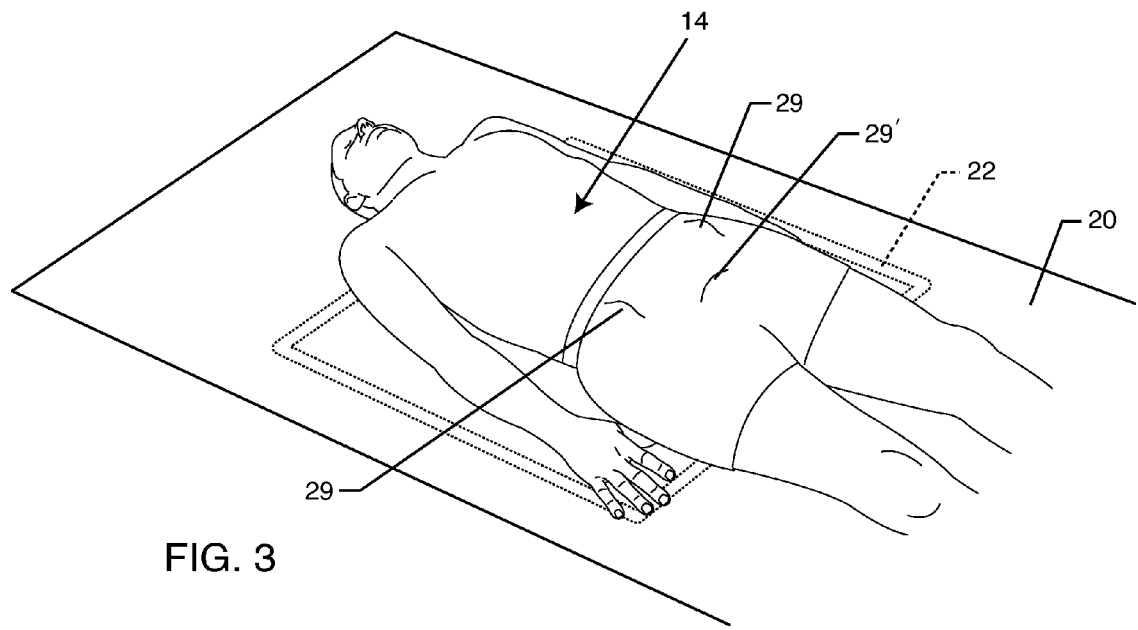
FIG. 3 is a top perspective view of a supine patient lying on an X-ray imaging table over a sheet of X-ray image film or recording media, and showing three bony prominences for use in patient interactive orientation of the alignment fixture depicted in FIGS. 1 and 2.

As shown in FIGS. 1 and 2, the alignment fixture 10 comprises, in one preferred form, a frame 26 constructed from a radio-transparent material such as a selected plastic or the like. The frame 26 comprises a tripod base having a respective trio of legs 27 terminating in a corresponding number of tripod feet 28 turned generally horizontally. These tripod feet 28 are adapted to rest respectively upon known patient landmarks associated generally with the anatomical region of interest, such as upon the anterior superior iliac spines 29 (FIGS. 3-5) and the symphysis pubis 29' in the case of a hip replacement patient. The tripod feet 28 are generally transparent, but each desirably includes a plurality of radio-opaque markers 30 such as dots or the like associated with general patient frame size markings to indicate the specific marker 30 to be rested upon the patient landmark in accordance with general frame size of the patient. Specifically, at least three markers 30 can be provided for suitably indicating a large-framed, a medium-framed, or a small-framed patient. Alternative and preferably increased numbers of the markers 30 can be used, preferably about 4-6 markers 30 on each tripod foot 28. In addition, these markers 30 may vary in size to provide a further indication of patient frame size.

The tripod base of the frame 26 is joined to an upright frame post 32 extending upwardly to a generally horizontally turned upper alignment arm 34. A transparent grid plate 36 is carried by this frame post 32 between the tripod base feet 28 and the upper alignment arm 34. The grid plate 36 carries the radio-opaque grid lines 24, preferably in a pattern comprising a pair of ruled grids 16 for respectively overlying the patient's hip joints when the alignment fixture 10 is properly positioned on the patient 14 (as described above) and aligned (as will be described in more detail).

The fixture 10 is held by the patient 14 in alignment relative to the X-ray beam source 18 (FIG. 6) by means of radio-opaque aiming marks 38 and 40 formed respectively on the upper alignment arm 34 and centrally on the grid plate 36. These aiming marks 38, 40 may comprise cross-hairs as shown, and are generally aligned one directly over the other, when the fixture feet 28 are rested upon the patient landmarks 29, 29' as previously described. With this orientation, the pair of ruled grids 16 on the grid plate 36 are properly positioned in overlying relation with the patient's hip joints. A light source such as a laser beam 41 (FIG. 6) generated substantially at the X-ray beam source 18 is normally used to align these aiming marks 38, 40. FIG. 7 shows the aiming marks 38, 40 in slight misalignment to indicate further positional adjustment is required for properly aligning the beam source 18, the alignment fixture 10, and the patient 14. FIG. 8 shows the aiming marks in proper positional alignment. With the feet 28 on the anatomic landmarks and with the aiming marks 38, 40 substantially aligned, the pelvis will be anatomically aligned with the X-ray beam. FIG. 9 comprising an actual X-ray image 12 shows the aiming marks 38, 40 in substantial vertical alignment.

Figure 4:
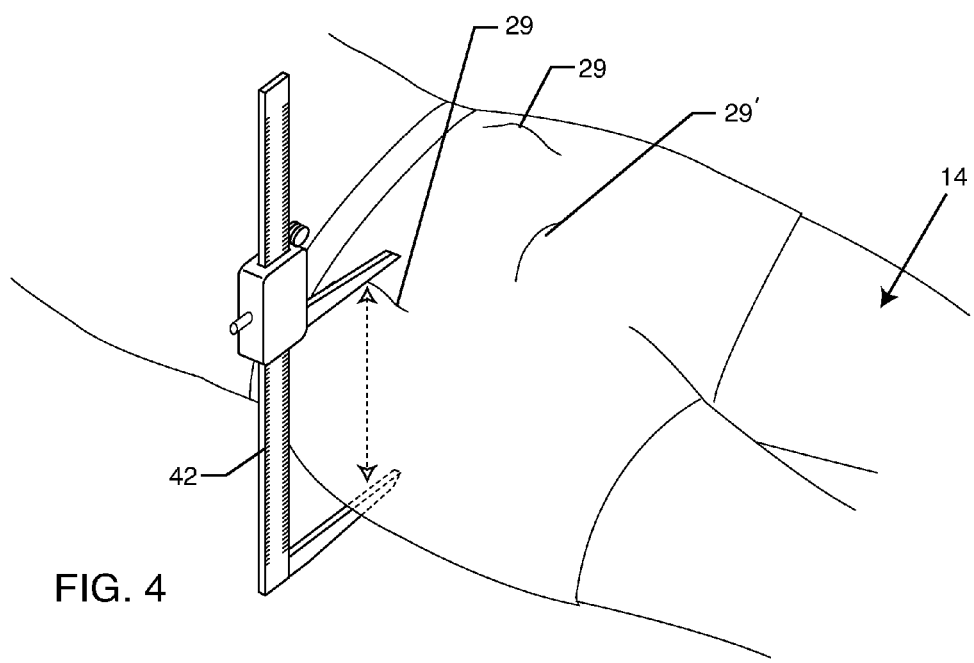
FIG. 4 is a fragmented and somewhat top perspective view of the supine patient shown in FIG. 3, and illustrating measurement of the patient thickness in a selected anatomical region, such as the pelvic region in the case of a hip replacement patient.
Figure 5:
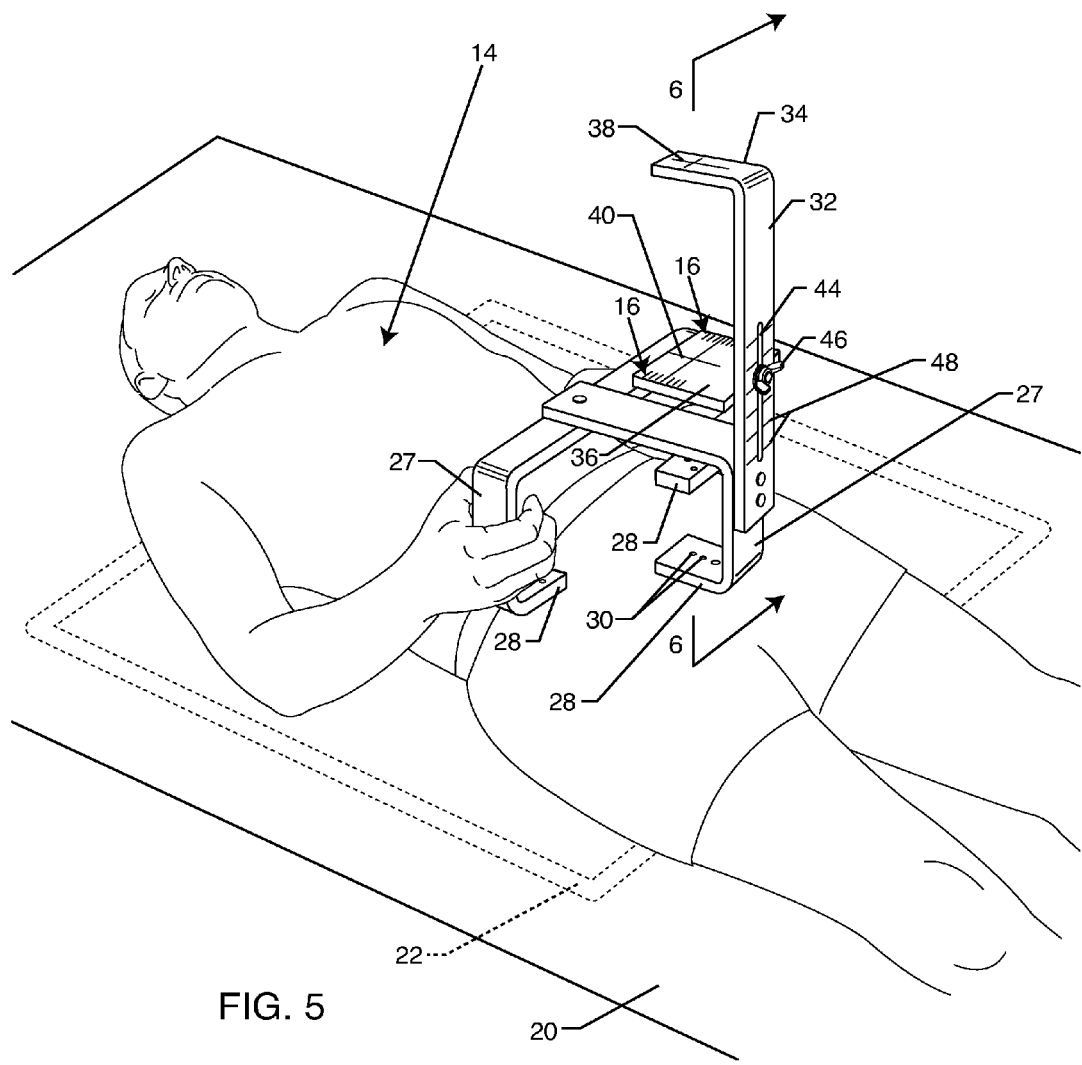
FIG. 5 is an enlarged and somewhat fragmented top perspective view of the supine patient similar to FIGS. 3 and 4, but illustrating placement of the alignment fixture of FIGS. 1 and 2 onto the supine patient.
Figure 6:
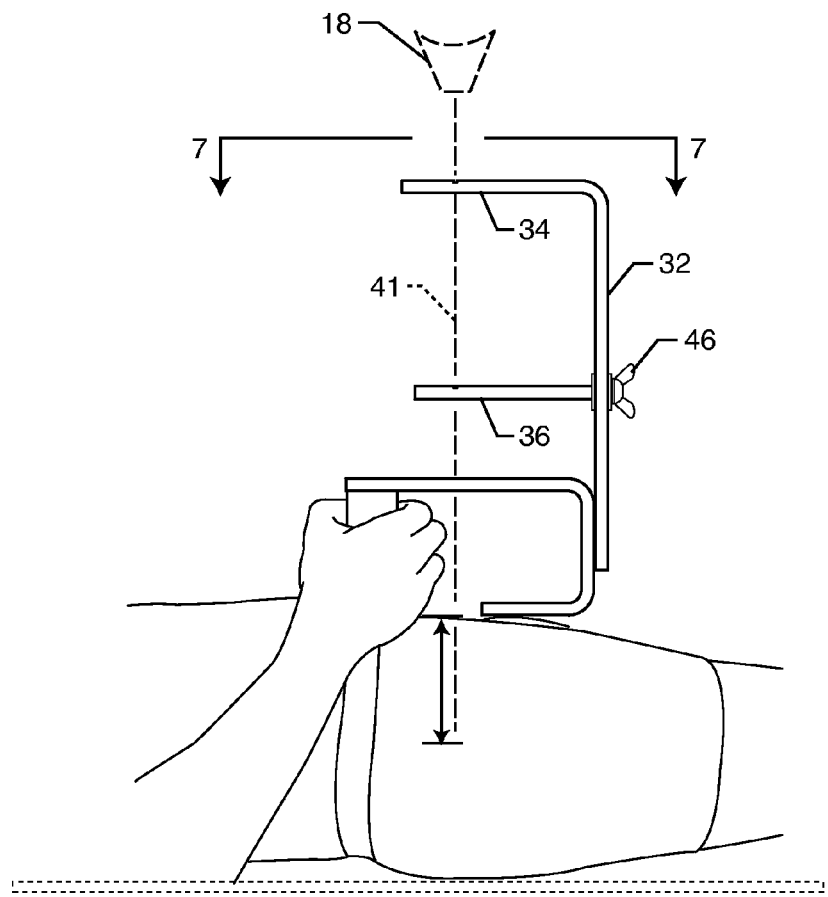
FIG. 6 is a vertical sectional view taken generally on the line 6-6 of FIG. 5.

The vertical position of the grid plate 36 is adjustably selected, as previously described, according to the specific thickness of the patient 14 in the selected anatomical region, such as the pelvic region in the case of a hip replacement patient. FIG. 4 shows a set of calipers 42 used to obtain a precise measurement of the patient's pelvic thickness (anterior superior spine to the X-ray table). With this measurement, the grid plate 36 is adjustably positioned along the vertical height of the frame post 32, as by means of the illustrative vertical slot 44 formed in the frame post 32 with a suitable fastener 46 that can be manually tightened when the selected vertical position of adjustment is reached. At least one scale 48 (FIG. 5) on the frame post 32 can be pre-printed according to patient pelvic thickness for use in adjustably setting the vertical position of the grid plate 36. This scale 48 may correspond with a standard distance (such as about 40 inches) from the beam source 18 (FIG. 6) to the X-ray film 22 (FIG. 5); if desired, different scales on opposite sides of the vertical slot 44 can be used for different standard source-to-film distances, such as an approximate 40 inches on one side of the slot 44, and an approximate 48 inches on the other side of the slot 44. Persons skilled in the art will recognize and appreciate that the specific markings of the scale or scales 48 may also vary according to the specific anatomical region of interest (such as the pelvic region as shown), and also according to the specific inter-line dimension as actually used on each ruled grid 16.

In a preferred and exemplary embodiment of the invention, the actual spacing between the grid lines 24 of each ruled grid 16 is selected to be about 0.6 cm., with an inter-line marking of about 1.0 cm. With this arrangement of the grid lines 24, the grid plate 36 is vertically positioned above the patient so that the grid lines 24 will be magnified by parallax to have an inter-line spacing of 1.0 cm. substantially at the center of the hip joints. Thereafter, the ruled grids 16 will be further magnified by parallax in a manner corresponding with the parallax magnification of the hip joints, whereby the resultant X-ray image will depict the overlying ruled grids 16 and the hip joints with known magnification. For example, if the hip joints are magnified 125% then the inter-line spacings between the ruled grid lines 24 will be 1.25 cm. The X-ray image 12 (FIG. 9) can thereby be scaled quickly and easily as needed, and with confidence, to select an appropriate-sized prosthesis for the patient 14. Such scaling of the image 12 can be performed manually, or, if the image 12 is digitally presented, by mere adjustment of the digital image controls.

A variety of modifications and improvements in and to the improved alignment fixture 10 and related method of use will be apparent to those persons skilled in the art. For example, persons skilled in the art will recognize and appreciate that the alignment fixture 10 may take different specific forms and the mathematics relating patient thickness to joint location and/or vertical grip plate adjustment, will vary according to the specific anatomical region of interest. Accordingly, no limitation on the invention is intended by way of the foregoing description and accompanying drawings, except as set forth in the appended claims.

What is claimed is:

1. In an X-ray image system having a patient table with an X-ray image film thereon and an overhead X-ray beam source spaced a known distance from the X-ray image film, an alignment fixture, comprising:
a frame formed generally from a radio-transparent material, said frame including a base having a plurality of legs adapted for respective seated placement on selected patient landmarks, and an upright post extending generally upwardly from said base, said upright post being joined to a generally horizontally turned upper alignment arm;
a radio-transparent grid plate carried by said upright post for vertical adjustment on said post between said base and said upper alignment arm in accordance with a measured patient thickness, said grid plate further including at least one radio-opaque ruled grid for overlying a selected patient anatomical region; and
radio-opaque aiming alignment marks carried respectively on said upper alignment arm and on said grid plate;
said at least one ruled grid including spaced grid markings which appear in an X-ray image with an apparent parallax image magnification corresponding with the parallax image magnification of the selected patient anatomical region, thereby permitting scaling and selection of an appropriate size prosthesis for surgical implantation.

2. The alignment fixture of claim 1 wherein said frame is formed from a radio-transparent plastic material.

3. The alignment fixture of claim 1 wherein said plurality of legs each terminate in a generally horizontally turned foot, and further wherein each of said feet includes a plurality of radio-opaque patient frame size markers.

4. The alignment fixture of claim 1 wherein said base comprises a tripod base having three legs, and further wherein said patient landmarks comprises known bony prominences on the patient.

5. The alignment fixture of claim 1 wherein said grid plate is formed from a radio-transparent plastic material.

6. The alignment fixture of claim 1 wherein said the selected patient anatomical region comprises the pelvic region, and wherein said at least one ruled grid comprises a pair of ruled grids for respectively overlying patient hip joints.

7. The alignment fixture of claim 1 wherein the alignment aiming marks comprise radio-opaque cross hairs.

8. The alignment fixture of claim 1 further comprising a laser light source disposed generally at the X-ray beam source for use in aligning the aiming alignment marks on the upper alignment arm and on the grid plate, prior to taking an X-ray image.

9. The alignment fixture of claim 1 further including at least one patient thickness scale on said post, said at least one grid plate being vertically adjustable relative to said patient thickness scale.

10. The alignment fixture of claim 9 wherein said at least one patient thickness scale comprises a pair of patient thickness scales associated respectively with different known distances between the X-ray beam source and the X-ray image film.

11. In an X-ray image system having a patient table with an X-ray image film thereon and an overhead X-ray beam source spaced a known distance from the X-ray image film, an alignment fixture, comprising:
a frame formed generally from a radio-transparent material, said frame including a tripod base having a plurality of three legs adapted for respective seated placement on selected patient bony prominences associated with the pelvic region of a patient, said bony prominences including the anterior superior iliac spines and the symphysis pubis of the patient, said frame further including an upright post extending generally upwardly from said base, said upright post being joined to a generally horizontally turned upper alignment arm;
a radio-transparent grid plate carried by said upright post for vertical adjustment thereon between said base and said upper alignment arm in accordance with a patient thickness scale on said post, said grid plate further including a pair of radio-opaque ruled grids for respectively overlying patient hip joints; and
radio-opaque aiming alignment marks carried respectively on said upper alignment arm and on said grid plate;
said pair of ruled grids each including spaced grid markings which appear in an X-ray image with an apparent parallax image magnification corresponding with the parallax image magnification of the patient pelvic region, thereby permitting scaling and selection of an appropriate size hip prosthesis for surgical implantation.

12. The alignment fixture of claim 11 wherein each of said legs terminates in a generally horizontally turned foot, and further wherein each of said feet includes a plurality of radio-opaque patient frame size markers.

13. The alignment fixture of claim 11 wherein the alignment aiming marks comprise radio-opaque cross hairs.

14. The alignment fixture of claim 11 further comprising a laser light source disposed generally at the X-ray beam source for use in aligning the aiming alignment marks on the upper alignment arm and on the grid plate, prior to taking an X-ray image.

15. A method of taking an X-ray image wherein the resultant X-ray image is scalable to determine an appropriate size prosthesis for subsequent surgical implantation, said method comprising the steps of:
positioning the patient on a table over an X-ray image film disposed at a known distance from an overhead X-ray beam source;
measuring the thickness of a selected anatomical patient region including a joint for subsequent prosthesis implantation;
placing an alignment fixture over the selected anatomical patient region between the patient and an X-ray beam source;
said alignment fixture comprising a radio-transparent frame including a base having a plurality of legs adapted for respective seated placement on selected patient landmarks, and an upright post extending generally upwardly from said base, said upright post being joined to a generally horizontally turned upper alignment arm;
vertically adjusting the position of a radio-transparent grid plate carried by said upright post for vertical adjustment thereon between said base and said upper alignment arm in accordance with a patient thickness scale on said post, said grid plate further including at least one radio-opaque ruled grid for overlying the selected anatomical patient region;
aligning radio-opaque aiming marks carried respectively on the upper alignment arm and on the grid plate; and
energizing the X-ray beam source to take the X-ray image, wherein the at least one ruled grid on the grid plate includes spaced grid markings which appear in the X-ray image with an apparent parallax image magnification corresponding with the parallax image magnification of a centerline of the selected patient anatomical region, thereby permitting scaling and selection of an appropriate size prosthesis for surgical implantation.

16. The method of claim 15 wherein each of the plurality of legs terminates in a generally horizontally turned foot, and further including the step of providing each of said feet with a plurality of radio-opaque patient frame size markers.

17. The method of claim 15 wherein the base comprises a tripod base having three legs for respective support on the patient landmarks comprising known bony prominences on the patient.

18. The method of claim 17 wherein the selected anatomical patient region comprises the pelvic region, and further wherein the bony prominences respectively comprise the anterior superior iliac spines and the symphysis pubis of the patient.

19. The method of claim 18 wherein the at least one ruled grid comprises a pair of ruled grids for respectively overlying patient hip joints.

20. The method of claim 15 wherein the radio-opaque aiming marks comprise radio-opaque cross hairs.

21. The method of claim 15 further including the step of comprising aligning the radio-opaque aiming marks with a laser light source disposed generally at the X-ray beam source.

22. The method of claim 15 further including the step of the patient holding the alignment fixture in place.

* * * * *